US012616611B2

(12) United States Patent
Locke

(10) Patent No.: US 12,616,611 B2
(45) Date of Patent: May 5, 2026

(54) FLUID INDICATORS FOR WOUND DRESSING SYSTEMS AND NEGATIVE PRESSURE TREATMENT

(71) Applicant: Solventum Intellectual Properties Company, Maplewood, MN (US)

(72) Inventor: Christopher Brian Locke, Bournemouth (GB)

(73) Assignee: Solventum Intellectual Properties Company, Maplewood, MN (US)

( * ) Notice: Subject to any disclaimer, the term of this patent is extended or adjusted under 35 U.S.C. 154(b) by 638 days.

(21) Appl. No.: 18/018,353

(22) PCT Filed: Jul. 20, 2021

(86) PCT No.: PCT/IB2021/056535
§ 371 (c)(1),
(2) Date: Jan. 27, 2023

(87) PCT Pub. No.: WO2022/023873
PCT Pub. Date: Feb. 3, 2022

(65) Prior Publication Data
US 2023/0285193 A1 Sep. 14, 2023

Related U.S. Application Data

(60) Provisional application No. 63/057,383, filed on Jul. 28, 2020.

(51) Int. Cl.
*A61F 13/00* (2024.01)
*A61F 13/0203* (2024.01)
(Continued)

(52) U.S. Cl.
CPC .... *A61F 13/00055* (2013.01); *A61F 13/0226* (2013.01); *A61F 13/025* (2013.01); *A61F 13/05* (2024.01); *A61M 1/91* (2021.05)

(58) Field of Classification Search
CPC ...... A61M 1/918; A61M 1/912; A61M 1/913; A61M 1/985; A61M 1/96; A61M 1/915; A61M 1/743; A61M 1/734
See application file for complete search history.

(56) References Cited

U.S. PATENT DOCUMENTS

| 1,355,846 A | 10/1920 | Rannells |
| 2,547,758 A | 4/1951 | Keeling |

(Continued)

FOREIGN PATENT DOCUMENTS

| AU | 550575 B2 | 3/1986 |
| AU | 745271 B2 | 3/2002 |

(Continued)

OTHER PUBLICATIONS

International Search Report and Written Opinion for Corresponding Application No. PCT/IB2021/056535, mailed Oct. 26, 2021.

(Continued)

*Primary Examiner* — Kim M Lewis

(57) ABSTRACT

An indicator, wound dressing system, and negative pressure wound treatment kit configured to provide near real-time, dynamic indication of the fluid status (e.g., fill level, fluid absorbency capacity) of an article is described according to various embodiments. The indicator for detecting a fluid status of a wound dressing may include at least (i) a top side comprising PVDF and one or more markings configured to show fluid levels (ii) a bottom side comprising a pattern-printed adhesive, and (iii) a buffer layer, wherein the buffer layer has a top side comprising a polyurethane film and a bottom side comprising a film retention adhesive. Methods of using the indicator, wound dressing system, and kit are also provided herein.

17 Claims, 6 Drawing Sheets

(51) Int. Cl.
   *A61F 13/0246*      (2024.01)
   *A61F 13/05*      (2024.01)
   *A61M 1/00*      (2006.01)

(56)        References Cited

U.S. PATENT DOCUMENTS

| | | | |
|---|---|---|---|
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |
| 4,419,097 | A | 12/1983 | Rowland |
| 4,465,485 | A | 8/1984 | Kashmer et al. |
| 4,475,909 | A | 10/1984 | Eisenberg |
| 4,480,638 | A | 11/1984 | Schmid |
| 4,525,166 | A | 6/1985 | Leclerc |
| 4,525,374 | A | 6/1985 | Vaillancourt |
| 4,540,412 | A | 9/1985 | Van Overloop |
| 4,543,100 | A | 9/1985 | Brodsky |
| 4,548,202 | A | 10/1985 | Duncan |
| 4,551,139 | A | 11/1985 | Plaas et al. |
| 4,569,348 | A | 2/1986 | Hasslinger |
| 4,605,399 | A | 8/1986 | Weston et al. |
| 4,608,041 | A | 8/1986 | Nielsen |
| 4,640,688 | A | 2/1987 | Hauser |
| 4,655,754 | A | 4/1987 | Richmond et al. |
| 4,664,662 | A | 5/1987 | Webster |
| 4,710,165 | A | 12/1987 | McNeil et al. |
| 4,733,659 | A | 3/1988 | Edenbaum et al. |
| 4,743,232 | A | 5/1988 | Kruger |
| 4,758,220 | A | 7/1988 | Sundblom et al. |
| 4,787,888 | A | 11/1988 | Fox |
| 4,826,494 | A | 5/1989 | Richmond et al. |
| 4,838,883 | A | 6/1989 | Matsuura |
| 4,840,187 | A | 6/1989 | Brazier |
| 4,863,449 | A | 9/1989 | Therriault et al. |
| 4,872,450 | A | 10/1989 | Austad |
| 4,878,901 | A | 11/1989 | Sachse |
| 4,897,081 | A | 1/1990 | Poirier et al. |
| 4,906,233 | A | 3/1990 | Moriuchi et al. |
| 4,906,240 | A | 3/1990 | Reed et al. |
| 4,919,654 | A | 4/1990 | Kalt |
| 4,941,882 | A | 7/1990 | Ward et al. |
| 4,953,565 | A | 9/1990 | Tachibana et al. |
| 4,969,880 | A | 11/1990 | Zamierowski |
| 4,985,019 | A | 1/1991 | Michelson |
| 5,037,397 | A | 8/1991 | Kalt et al. |
| 5,086,170 | A | 2/1992 | Luheshi et al. |
| 5,092,858 | A | 3/1992 | Benson et al. |
| 5,100,396 | A | 3/1992 | Zamierowski |
| 5,134,994 | A | 8/1992 | Say |
| 5,149,331 | A | 9/1992 | Ferdman et al. |
| 5,167,613 | A | 12/1992 | Karami et al. |
| 5,176,663 | A | 1/1993 | Svedman et al. |
| 5,215,522 | A | 6/1993 | Page et al. |
| 5,232,453 | A | 8/1993 | Plass et al. |
| 5,261,893 | A | 11/1993 | Zamierowski |
| 5,278,100 | A | 1/1994 | Doan et al. |
| 5,279,550 | A | 1/1994 | Habib et al. |
| 5,298,015 | A | 3/1994 | Komatsuzaki et al. |
| 5,342,376 | A | 8/1994 | Ruff |
| 5,344,415 | A | 9/1994 | DeBusk et al. |
| 5,358,494 | A | 10/1994 | Svedman |
| 5,437,622 | A | 8/1995 | Carion |
| 5,437,651 | A | 8/1995 | Todd et al. |
| 5,527,293 | A | 6/1996 | Zamierowski |
| 5,549,584 | A | 8/1996 | Gross |
| 5,556,375 | A | 9/1996 | Ewall |
| 5,607,388 | A | 3/1997 | Ewall |
| 5,636,643 | A | 6/1997 | Argenta et al. |
| 5,645,081 | A | 7/1997 | Argenta et al. |
| 6,071,267 | A | 6/2000 | Zamierowski |
| 6,135,116 | A | 10/2000 | Vogel et al. |
| 6,241,747 | B1 | 6/2001 | Ruff |
| 6,287,316 | B1 | 9/2001 | Agarwal et al. |
| 6,345,623 | B1 | 2/2002 | Heaton et al. |
| 6,488,643 | B1 | 12/2002 | Tumey et al. |
| 6,493,568 | B1 | 12/2002 | Bell et al. |
| 6,553,998 | B2 | 4/2003 | Heaton et al. |
| 6,814,079 | B2 | 11/2004 | Heaton et al. |
| 7,846,141 | B2 | 12/2010 | Weston |
| 8,062,273 | B2 | 11/2011 | Weston |
| 8,216,198 | B2 | 7/2012 | Heagle et al. |
| 8,251,979 | B2 | 8/2012 | Malhi |
| 8,257,327 | B2 | 9/2012 | Blott et al. |
| 8,398,614 | B2 | 3/2013 | Blott et al. |
| 8,449,509 | B2 | 5/2013 | Weston |
| 8,529,548 | B2 | 9/2013 | Blott et al. |
| 8,535,296 | B2 | 9/2013 | Blott et al. |
| 8,551,060 | B2 | 10/2013 | Schuessler et al. |
| 8,568,386 | B2 | 10/2013 | Malhi |
| 8,679,081 | B2 | 3/2014 | Heagle et al. |
| 8,834,451 | B2 | 9/2014 | Blott et al. |
| 8,926,592 | B2 | 1/2015 | Blott et al. |
| 9,017,302 | B2 | 4/2015 | Vitaris et al. |
| 9,198,801 | B2 | 12/2015 | Weston |
| 9,211,365 | B2 | 12/2015 | Weston |
| 9,289,542 | B2 | 3/2016 | Blott et al. |
| 2002/0077661 | A1 | 6/2002 | Saadat |
| 2002/0115951 | A1 | 8/2002 | Norstrem et al. |
| 2002/0120185 | A1 | 8/2002 | Johnson |
| 2002/0143286 | A1 | 10/2002 | Tumey |
| 2014/0163491 | A1 | 6/2014 | Schuessler et al. |
| 2015/0080788 | A1 | 3/2015 | Blott et al. |
| 2015/0351970 | A1* | 12/2015 | Dagger ............ A61F 13/00055 |
| | | | 604/361 |
| 2018/0071428 | A1 | 3/2018 | Gerdes et al. |
| 2019/0336343 | A1* | 11/2019 | Etchells ................. A61F 13/42 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2195255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |

(56)                    References Cited

FOREIGN PATENT DOCUMENTS

| WO | 87/04626 A1 | 8/1987 |
|----|-------------|--------|
| WO | 90/010424 A1 | 9/1990 |
| WO | 93/009727 A1 | 5/1993 |
| WO | 94/20041 A1 | 9/1994 |
| WO | 96/05873 A1 | 2/1996 |
| WO | 97/18007 A1 | 5/1997 |
| WO | 99/13793 A1 | 3/1999 |
| WO | 2019/030384 A2 | 2/2019 |

OTHER PUBLICATIONS

Louis C. Argenta, Md and Michael J. Morykwas, Phd; Vacuum-Assisted Closure: A New Method for Wound Control and Treatment: Clinical Experience; Annals of Plastic Surgery; vol. 38, No. 6, Jun. 1997; pp. 563-576.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, Md et al.: Negative-Pressure Dressings as a Bolster for Skin Grafts; Annals of Plastic Surgery, vol. 40, No. 5, May 1998, pp. 453-457; Lippincott Williams & Wilkins, Inc., Philidelphia, PA, USA.

John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.

S.E. Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, Md., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. Yu.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al;"Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björm et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovi?, V. ? uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C.® Therapy Clinical Guidelines: A Reference Source for Clinicians; Jul. 2007.

* cited by examiner

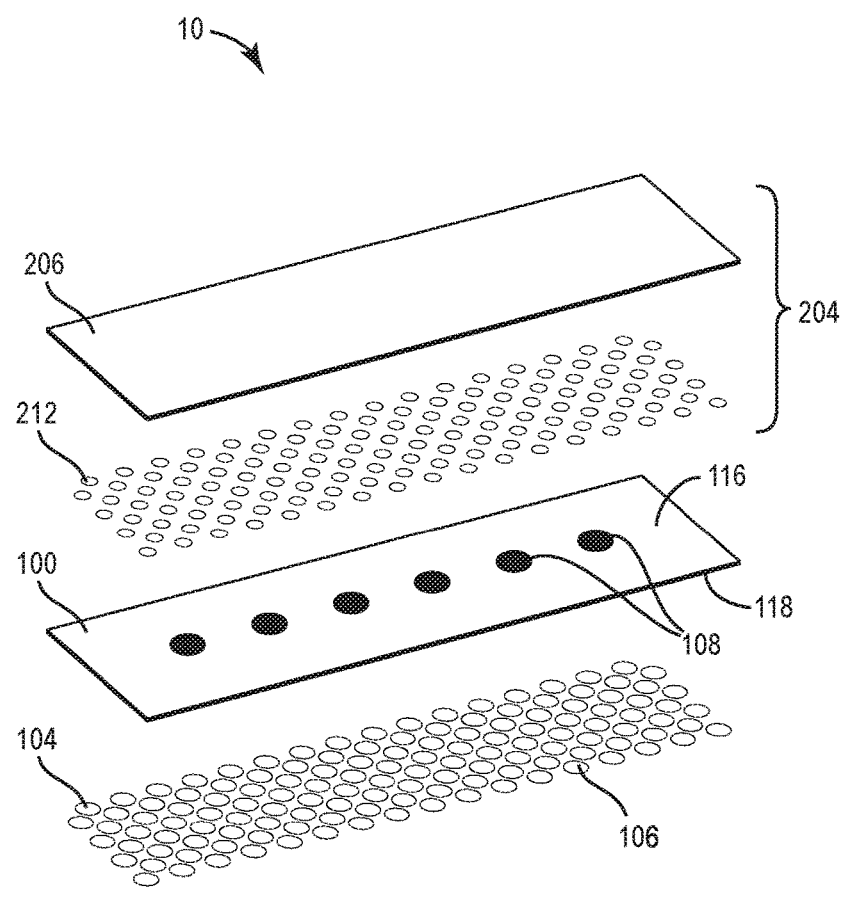
FIG. 2
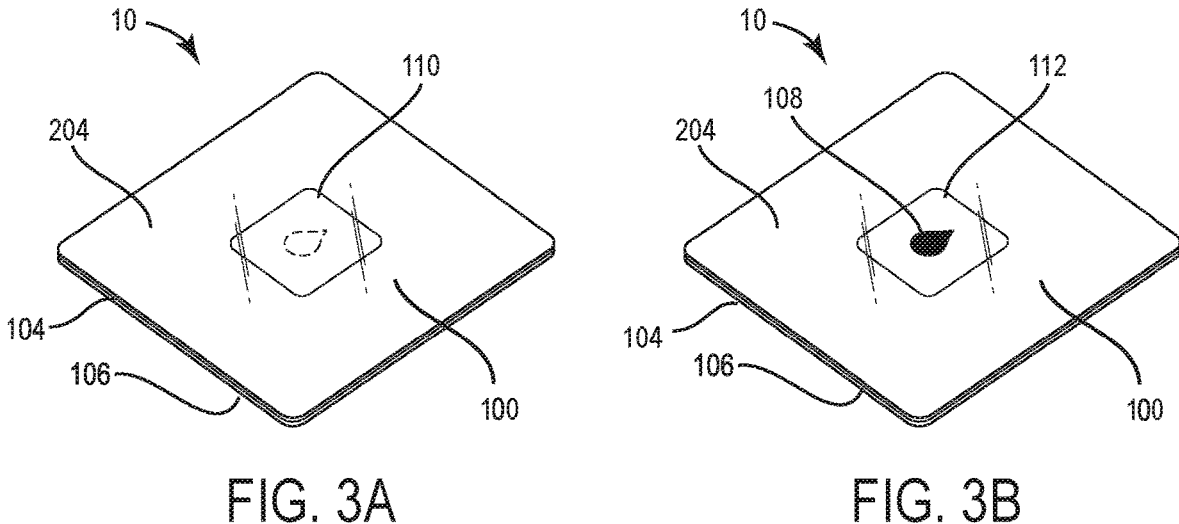
FIG. 3A                    FIG. 3B

FLUID INDICATORS FOR WOUND DRESSING SYSTEMS AND NEGATIVE PRESSURE TREATMENT

CROSS-REFERENCE TO RELATED APPLICATIONS

This application claims the benefit of priority to U.S. Provisional Application No. 63/057,383, filed on Jul. 28, 2020, which is incorporated herein by reference in its entirety.

FIELD OF THE INVENTION

The present disclosure relates generally to an indicator for a wound dressing configured to monitor a fluid level status of the wound dressing and/or the tissue to which the wound dressing is attached.

BACKGROUND

Existing wound dressing systems are usually configured to transition between a first visual state wherein wound exudate or fluids are not visible to a second state wherein the wound exudate is visible to an attending medical professional or patient. However, these same systems are not capable of reversing from this transition and returning to the first visual state if wound exudate or other fluids evaporate or are removed. The inability to reversibly transition limits the wound dressings to a single use, which can lead to significant waste over the course of a treatment period every time wound fluids collect in the dressing.

Developing a system that is able to selectively reverse states upon exposure to wound fluids requires accurate fluid indicators embedded in the dressing so as to allow for visualization of the fluids without removal of the dressing. In certain instances, these indicators may improperly leach silicone oils or gels from adjacent wicking or dressing layers, which can lead to premature transition and incorrectly indicate the presence of wound fluid or excessively hydrated skin. This leaching effect may happen over time, resulting in prematurely switched indicators during shelf-life storage. Thus, there exists a need for a wound fluid indicator and system capable of selectively transitioning upon exposure to wound fluids with high accuracy and sensitivity.

SUMMARY

The present disclosure overcomes the drawbacks of previously-known systems by providing fluid indicators, wound dressings, wound dressing systems, and methods of use.

In one aspect of the present disclosure, an indicator for detecting the fluid status of a wound dressing repair is described. The indicator may comprise, or consist essentially of, or yet further consist of (i) a top side comprising polyvinylidene difluoride (PVDF) and one or more markings configured to show fluid levels, (ii) a bottom side comprising a pattern-printed adhesive; and (iii) a buffer layer, wherein the buffer layer comprises a top side comprising a polyurethane film and a bottom side comprising a film retention adhesive. In a first state, the markings of the indicator may be blocked by the top side comprising PVDF and not visible to a user under ambient or natural light. In a second state, the markings may be visible through the top side under ambient or natural light. In a third state, the markings may again be blocked by the top side and not visible to a user under ambient or natural light, the third state occurring at a point in time subsequent to the second state.

In some embodiments, the first state is representative of an absence of absorbed wound fluid, the second state is representative of a presence of absorbed wound fluid, and the third state is representative of a reduction by evaporation of the wound fluid present in the second state. In some embodiments, the top side may be formed from a porous, hydrophilic structure defined by a plurality of fibers.

Additionally or alternatively, in certain embodiments, in the first state, the fibers have a first refractive index and in the second state the fibers have a second refractive index that is greater than the first refractive index. In some embodiments, the indicator may be exposed to a fluid in the second state, the material from which the fibers are formed being selected such that, when exposed to the fluid, the second refractive index of the fibers is substantially the same as the refractive index of the fluid.

In accordance with another aspect of the disclosure, a wound dressing system is described. The wound dressing system may comprise, or consist essentially of, or yet further consist of: (i) an uncrosslinked silicone polymer adhesive; (ii) an indicator comprising a top side, a bottom side, and a buffer layer, wherein the top side comprises polyvinylidene difluoride (PVDF) and one or more markings configured to show fluid levels along a lower surface thereof, the bottom side comprises a pattern-printed adhesive; and the buffer layer is positioned between the silicone polymer adhesive and the indicator layer, wherein the buffer layer comprises a top side comprising a polyurethane film and a bottom side comprising a film retention adhesive.

In the wound dressing system, the indicator further may include a layer of wicking material. Additionally or alternatively, the wicking material may be designed to not wick at least one of silicone oil, silicone gel, or a silicone derivative that when contacted with PVDF results in a change of states. In certain embodiments, the wicking material may be configured to wick exudate from a wound and the buffer layer may be sized to prevent wicking from the uncrosslinked silicone polymer adhesive.

Additionally or alternatively, in certain embodiments of the wound dressing system, (i) in a first state, the marking may be blocked by the top side PVDF and not visible to a user under ambient or natural light; (ii) in a second state, the marking may be visible through the top side under ambient or natural light; and (iii) in a third state, the marking may be blocked by the top side and not visible to a user under ambient or natural light, the third state occurring at a point in time subsequent to the second state. In some embodiments of the wound dressing system, the first state is representative of an absence of absorbed wound fluid, the second state is representative of a presence of absorbed wound fluid, and the third state is representative of a reduction by evaporation of the wound fluid present in the second state.

Additionally or alternatively, the indicator may be configured to reversibly undergo a first transition between a first visual configuration and a second visual configuration in response to the occurrence of a first state in which the indicator is exposed to a first quantity of fluid, and to undergo a second transition between the second visual configuration and the first visual configuration in response to the occurrence of a second state in which the indicator is exposed to a second quantity of fluid. The second quantity of fluid may correspond to a quantity of fluid to which the indicator was exposed immediately prior to the occurrence of the first state. In some embodiments, the indicator further may have a portion comprising a fluid-impermeable material with a high moisture vapor transmission rate. In certain embodiments of the wound dressing system, the buffer layer may be less than about 20 μm in thickness. In certain exemplary embodiments, the buffer layer is about 10 μm in thickness. Alternatively or additionally, the pattern-printed adhesive may be an acrylate or polyurethane adhesive. The pattern-printed adhesive also may be spaced to create a direct contact area of over 60% between the buffer layer and the indicator and only about 40% coverage of adhesive to retain the buffer layer in place. The pattern-printed adhesive may, in some embodiments, be a pattern of adhesive dots, lines, or grids that achieve a direct contact area of over 60% between the buffer layer and the indicator and only about 40% coverage of adhesive to retain the buffer layer in place. The ratio of 60% direct contact area to 40% adhesive coverage can ensure sufficient moisture vapor transmission rate (MVTR) to allow for drying and re-setting of the indicator.

In some embodiments, the buffer layer may be spray coated to the top side of the indicator in lieu of a film retention adhesive. The top side of the indicator may further include a polyurethane film extruded onto the PVDF in a reel-to-reel process comprising thermal bonds between the two layers before an adhesive is added. The PVDF further may include a hydrophobic coating.

In accordance with yet another aspect of the present disclosure, a method of monitoring a fluid status using a wound dressing system is described. The method may comprise, or consist essentially of, or vet further consist of providing the indicator in fluid communication with a wicking layer of the wound dressing; exposing the wound dressing system to a first amount of fluid during the first state; exposing the wound dressing system to a second amount of fluid during the second state; and exposing the wound dressing system to a third amount of fluid during the third state; wherein in the first state, a marking provided along the indicator is not visible to a user under ambient or natural light; wherein in the second state, the marking is visible to a user under ambient or natural light; and wherein in the third state, the marking is not visible to a user under ambient or natural light, the third state occurring at a point in time subsequent to the second state.

In some embodiments of the method, the first state corresponds to an initial application of the wound dressing and indicator to a wound; the second state occurs in response to the wound dressing being exposed to fluid; and the third state occurs in response to some or all of the fluid to which the wound dressing was exposed to in the second state being removed from or evaporated from the wound dressing.

In accordance with yet another aspect of the present disclosure, a negative pressure wound treatment kit is described. The wound treatment kit may comprise, or consist essentially of, or vet further consist of a negative pressure source: a wound dressing configured to be attached to a patient; and a conduit configured to fluidly couple the negative pressure source to a treatment space defined underneath the wound dressing upon application of the wound dressing to the patient; wherein the wound dressing comprises: (i) an uncrosslinked silicone polymer adhesive; (ii) an indicator comprising a top side, a bottom side, and a buffer layer, wherein the top side comprises polyvinylidene difluoride (PVDF) and one or more markings configured to show fluid levels along a lower surface thereof, the bottom side comprises a pattern-printed adhesive, and the buffer layer is positioned between the silicone polymer adhesive and the indicator layer, wherein the buffer layer comprises a top side comprising a polyurethane film and a bottom side comprising a film retention adhesive.

In some embodiments of the negative pressure wound treatment kit, the wound dressing further comprises: a manifolding layer configured to distribute negative pressure generated by the negative pressure source to a wound located beneath the wound dressing; and a drape layer configured to secure the manifolding layer relative to the patient; wherein a lower surface of the indicator directly contacts the manifolding layer.

In some embodiments of the negative pressure wound treatment kit, the wound dressing further includes a manifolding layer configured to distribute negative pressure generated by the negative pressure source to a wound located beneath the wound dressing; and a drape layer configured to secure the manifolding layer relative to the patient, an outer perimeter of the drape layer defining a border that extends outwards relative to an outer perimeter of the manifolding layer and is configured to be secured to the patient, wherein the indicator is positioned at a location along the border defined by the drape layer.

In some embodiments of the negative pressure wound treatment kit, an upper surface of the indicator directly contacts a lower surface of the drape layer and a lower surface of the indicator directly contacts a portion of the skin of the patient surrounding the wound upon application of the wound dressing to the patient. The indicator further may have an upper surface directly contacting a lower surface of the drape layer and a lower surface of the indicator directly contacting an upper surface of a wound interface layer. Additionally or alternatively, the wound treatment kit further may include a connector configured to be sealed around an opening formed in the drape layer of the wound dressing to fluidly couple the negative pressure source to the wound dressing, wherein the indicator is positioned between an upper surface of the drape layer and a lower surface of the connector.

BRIEF DESCRIPTION OF THE DRAWINGS

FIG. 2 shows an exemplary expanded view of the indicator with pattern-printed application adhesive on bottom and buffer layer with retention adhesive on top.

FIG. 3A illustrates one embodiment of an indicator and buffer layer in a first state wherein the indicator is not detecting wound exudate. FIG. 3B shows an indicator and buffer layer in a second state wherein the indicator is detecting wound exudate and the markings are visible through the top side under ambient or natural light.

US 12,616,611 B2

5

Figures 6A, 6B, 6C:
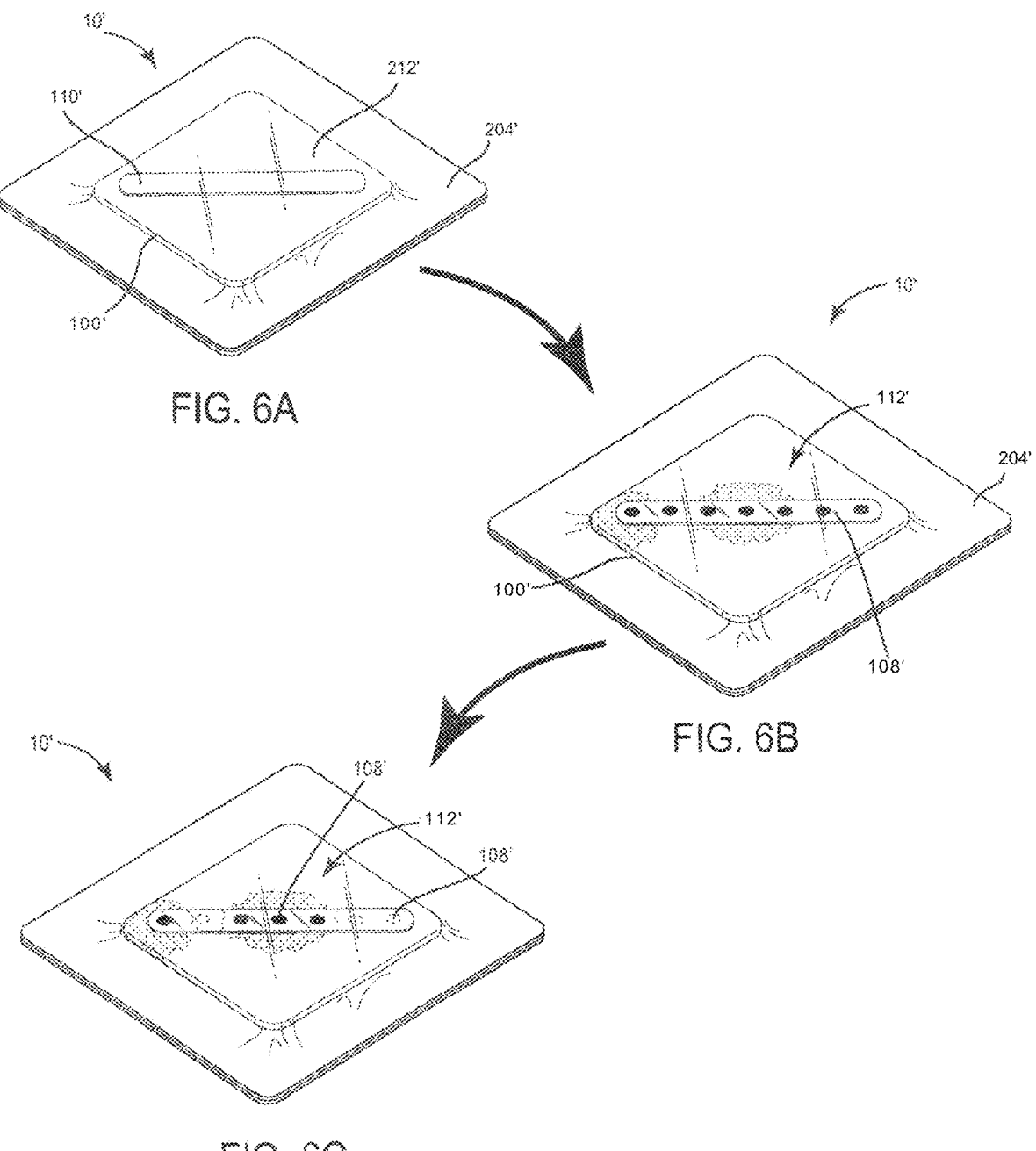

FIG. 6A-6C illustrates a method of treatment wherein a clinician or user may visualize an indicator and buffer layer reversibly transitioning from a first state (FIG. 6A) wherein the markings are not visible, to a second state where, when contacted by wound fluid or exudate, the markings become visible (FIG. 6B), and then to a third state (FIG. 6C) wherein the wound fluid or exudate is evaporating and the indicator marks are once again being rendered not visible.

Figure 7A:
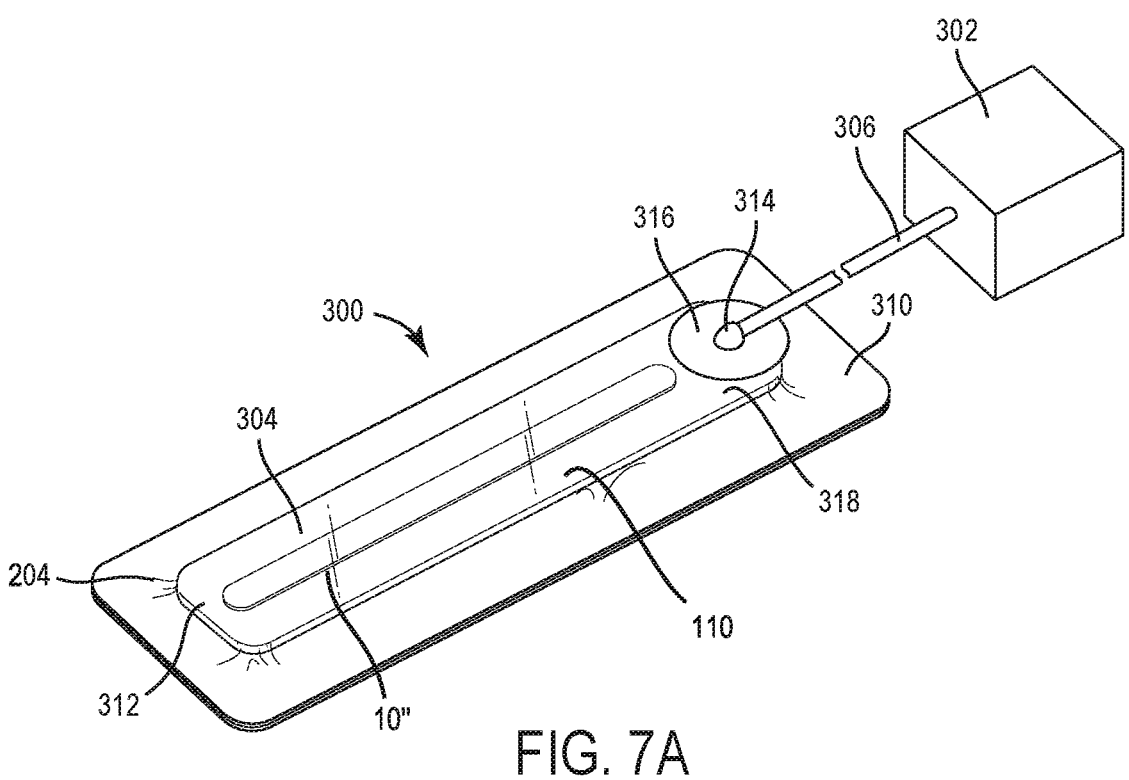
Figure 7B:
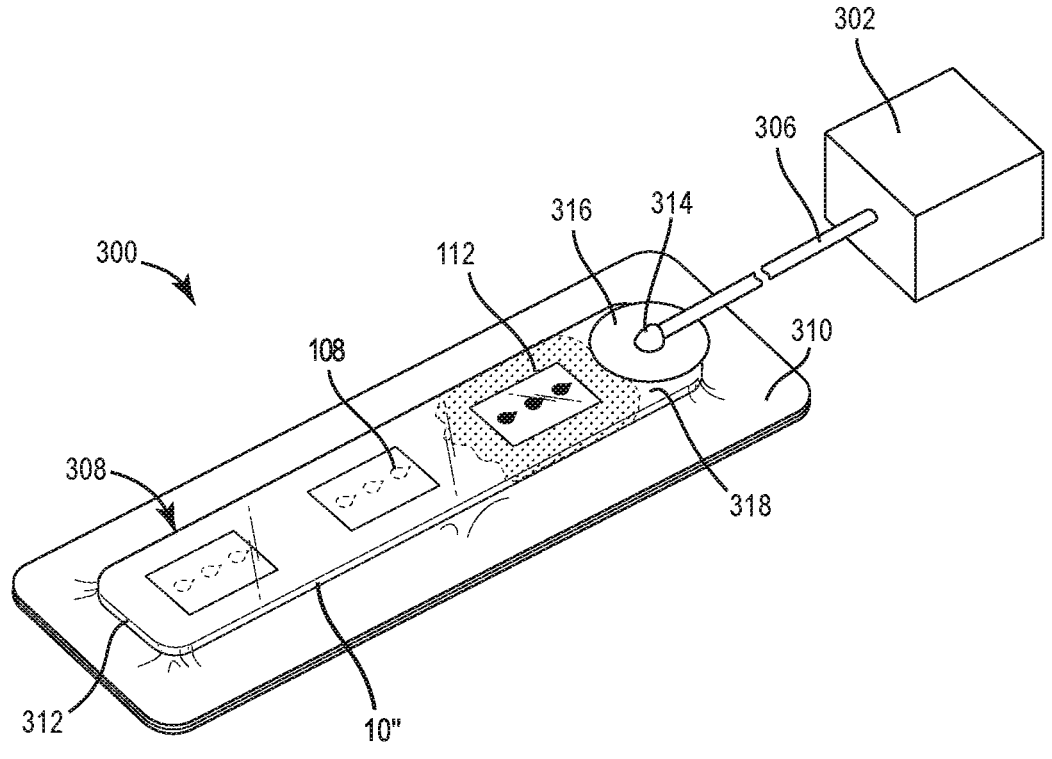

FIG. 7A-7B shows a negative pressure wound treatment kit. FIG. 7A depicts the kit in a first state wherein the markings of the indicator and buffer layer are not visible and wound exudate is not present. FIG. 7B shows a second state wherein the markings of the indicator and buffer layer are visible when wound exudate or fluid is present.

DETAILED DESCRIPTION

Before turning to the figures, which illustrate certain exemplary embodiments in detail, it should be understood that the present disclosure is not limited to the details or methodology set forth in the description or illustrated in the figures. It should also be understood that the terminology used herein is for the purpose of description only and should not be regarded as limiting.

Definitions

Unless defined otherwise, all technical and scientific terms used herein generally have the same meaning as commonly understood by one of ordinary skill in the art to which this technology belongs. As used in this specification and the appended claims, the singular forms "a". "an" and "the" include plural referents unless the content clearly dictates otherwise. For example, reference to "a cell" includes a combination of two or more cells, and the like. Generally, the nomenclature used herein and the laboratory procedures in cell culture, molecular genetics, organic chemistry, analytical chemistry and nucleic acid chemistry and hybridization described below are those well-known and commonly employed in the art.

As used herein, the term "about" in reference to a number is generally taken to include numbers that fall within a range of 1%, 5%, or 10% in either direction (greater than or less than) of the number unless otherwise stated or otherwise evident from the context (except where such number would be less than 0% or exceed 100% of a possible value).

Referring generally to the figures, an indicator, wound dressing system, and negative pressure wound treatment kit configured to provide near real-time, dynamic indication of the fluid status (e.g., fill level, fluid absorbency capacity, etc.) of an article is described according to various embodiments.

Indicators

Figure 1:
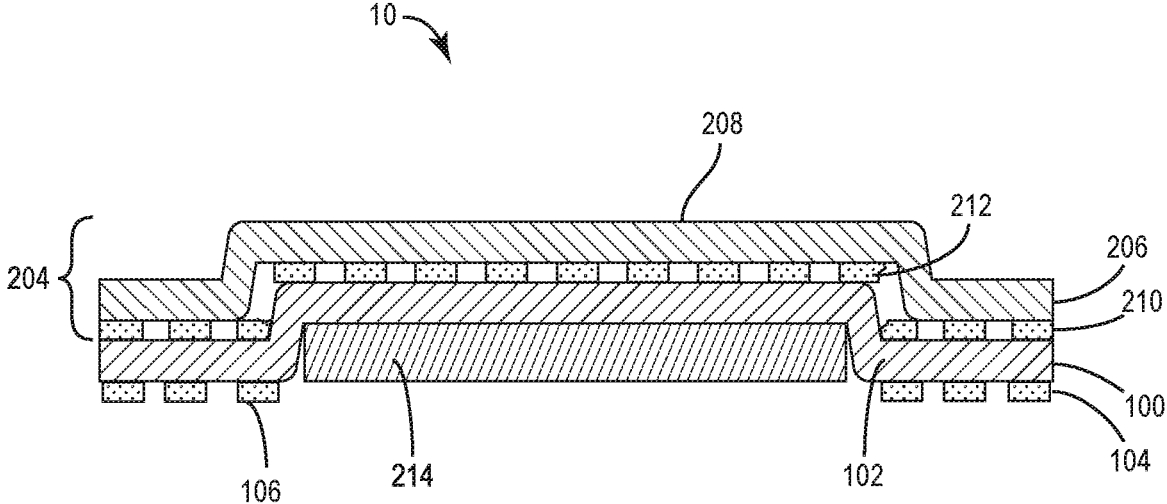
FIG. 1 shows an exemplary cross-sectional view of the indicator in an embodiment having a top side comprising a PVDF layer, a bottom side comprising a pattern-printed adhesive, and a buffer layer further having a top side comprising a polyurethane film and a bottom side comprising a film retention adhesive.

Referring to FIG. 1, an exemplary indicator 10 for detecting a fluid status of a wound dressing in accordance with the principles of the present disclosure is described. Indicator 10 may include top side 100 comprising polyvinylidene difluoride 102 (PVDF) and one or more markings 108 (shown in FIG. 2) configured to show fluid levels, and bottom side 104 comprising pattern-printed adhesive 106. The indicator 10 is configured and designed to display multiple would fluid or exudate states (e.g., fill level, fluid absorbency capacity, etc.). Referring to FIG. 3A, in a first state 110, markings 108 may be blocked by the top side 100 comprising PVDF 102 and not visible to a user under ambient or natural light. Referring to FIG. 3B, in a second state 112, markings 108 are visible through top side 100 under ambient or natural light. In a third state, markings 108 are blocked by top side 100 and not visible to a user under ambient or natural light. In some embodiments, the third state may occur at a point in time subsequent to second state 112 and visually appears similar to first state 110. Referring again to FIG. 1, indicator 10 further may include buffer layer 204 which includes top side 206 comprising a polyurethane film 208 and a bottom side 210 comprising a film retention adhesive 212.

FIG. 2 shows an exemplary expanded view of indicator 10 with pattern-printed application adhesive 106 on bottom side 104 and buffer layer 204 with film retention adhesive 212 on top side 206. Top side 100 of indicator 10 may be formed from a porous, hydrophilic structure 116 defined by a plurality of fibers 118. Fibers 118 may have a first refractive index in first state 110, and in second state 112 fibers 118 may have a second refractive index that is greater than the first refractive index. A material from which fibers 118 are formed may also be selected such that, when exposed to wound fluids WF, the second refractive index of fibers 118 is substantially the same as the refractive index of the fluid.

Referring to FIG. 3A, in certain exemplary embodiments, first state 110 is representative of an absence of absorbed wound fluid WF. In FIG. 3B, second state 112 is representative of a presence of absorbed wound fluid WF, and the third state is representative of a reduction by evaporation of the wound fluid WF present in second state 112.

Wound Dressing System

Figure 4:
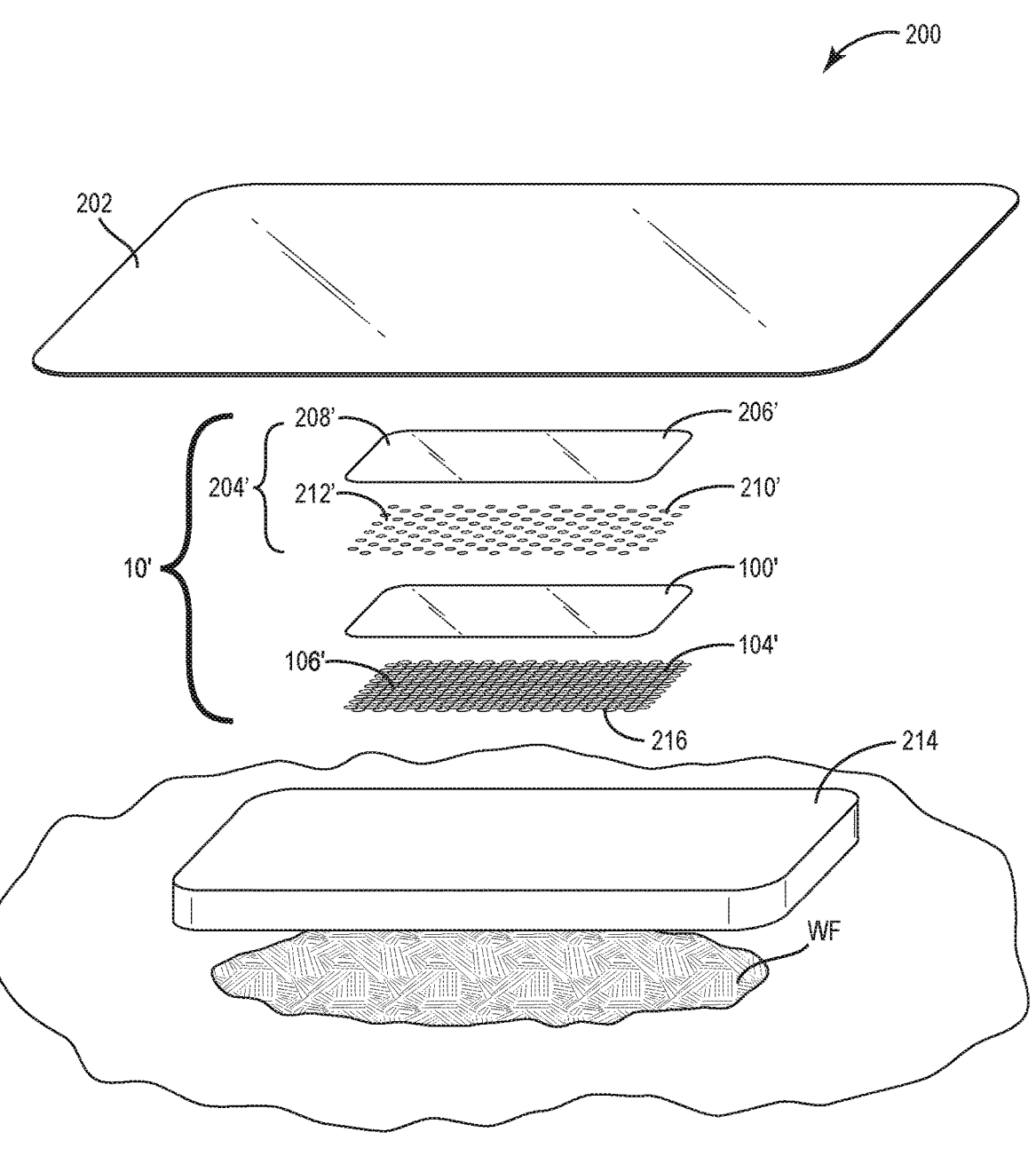
FIG. 4 shows an expanded view of an exemplary wound dressing system comprising an absorbent layer or wicking material, an indicator, a buffer layer, and a silicone polymer adhesive.

Referring now to FIG. 4, wound dressing system 200 in accordance with the principles of the present disclosure is described. Wound dressing system 200 may include: (i) an uncrosslinked silicone polymer adhesive 202; (ii) indicator 10' comprising top side 100' and bottom side 104' wherein top side 100' comprises polyvinylidene difluoride (PVDF) and one or more markings 108' configured to show fluid levels and bottom side 104' comprises pattern-printed adhesive 106'; and (iii) buffer layer 204' positioned between silicone polymer adhesive 202 and indicator 10', wherein buffer layer 204' comprises a top side 206' comprising a polyurethane film 208' and a bottom side 210' comprising a film retention adhesive 212'.

In some embodiments of wound dressing system 200, indicator 10' further may include a layer of wicking material 214. In preferred embodiments, wicking material 214 does not wick at least one of silicone oil, silicone gel, or a silicone derivative that might cause the indicator to change states. Wicking material 214 may be configured to wick exudate from a wound and buffer layer 204' may be sized to prevent wicking from uncrosslinked silicone polymer adhesive 202.

Figure 5A:
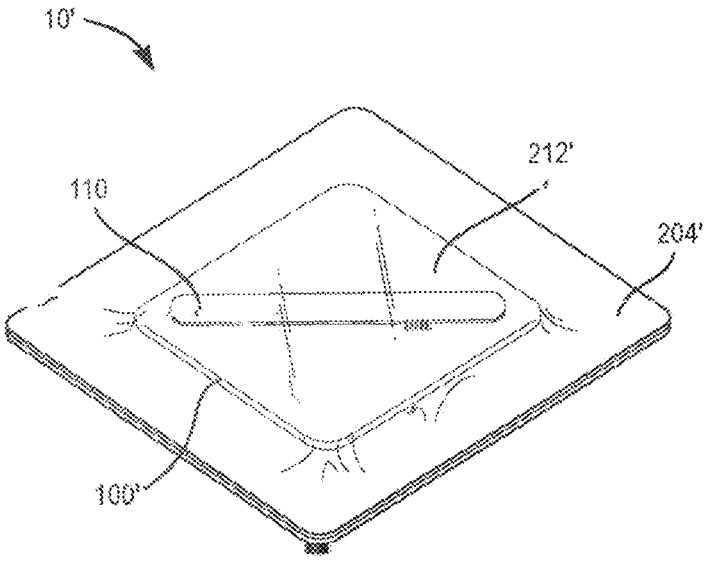
FIG. 5A shows an indicator and buffer layer wherein the indicator markings are situated sequentially along an axis and are in a first state wherein the markings are not visible.
Figure 5B:
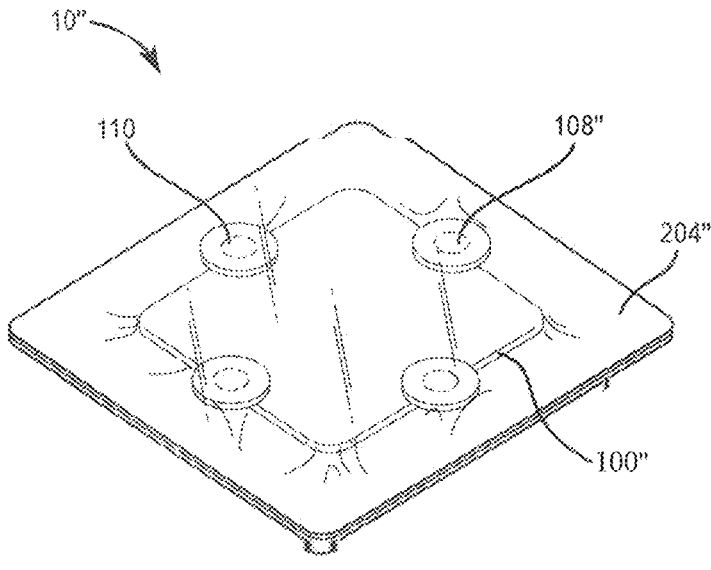
FIG. 5B shows an indicator and buffer layer wherein the indicator markings are separated along orthogonal axes and distanced to collect fluids from all corners of the top layer of the wound dressing. The markings, here, are again in a first state and are not visible.

As shown in FIG. 5A, wound dressing system 200 may appear with indicator 10' in first state 110, wherein markings 108' (shown in FIG. 4) are blocked by top side 100' and PVDF is not visible to a user under ambient or natural light. In second state 112, however, the marking 108' of the wound dressing system may be visible through top side 100' under ambient or natural light. Further, in a third state, marking 108' may be blocked by top side 100' and not visible to a user under ambient or natural light, the third state occurring at a point in time subsequent to the second state 112. In some embodiments, the third state may appear visually similar to first state 110. In certain embodiments, first state 110 may be representative of an absence of absorbed wound fluid, second state 112 may be representative of the presence of absorbed wound fluid, and the third state is representative of a reduction by evaporation of the wound fluid that was present in second state 112. FIG. 5B shows an alternative embodiment comprising indicator 10" and buffer layer 204", wherein indicator markings 108" are separated along orthogonal axes and distanced to collect fluids from all corners of the top layer of the wound dressing. The markings, here, are again in a first state 110 and are not visible.

Indicator 10' of wound dressing system 200 may be configured to reversibly undergo a first transition between a first visual configuration and a second visual configuration. The transition may occur in response to exposure to a first quantity of fluid. Indicator 10' may further undergo a second transition between the second visual configuration and the first visual configuration in response to the occurrence of second state 112' in which the indicator is exposed to a second quantity of fluid. In some embodiments of wound dressing system 200, the second quantity of fluid corresponds to a quantity of fluid to which the indicator was exposed immediately prior to the occurrence of the first state. In certain embodiments, indicator 10' further may include a portion having a fluid-impermeable material having a high moisture vapor transmission rate.

Buffer layer 204' is configured to be thin enough to not appreciably affect the moisture vapor transmission rate of wound dressing system 200. In some embodiments, buffer layer 204' is less than about 20 μm in thickness. In some embodiments, buffer layer 204' may be any of about 1 μm, 2 μm, 3 μm, 4 μm, 5 μm, 6 μm, 7 μm, 8 μm, 9 μm, 10 μm, 11 μm, 12 μm, 13 μm, 14 μm, 15 μm, 16 μm, 17 μm, 18 μm, 19 μm, 20 μm, 21 μm, 22 μm, 23 μm, 24 μm, or 25 μm in thickness. In certain embodiments, buffer layer 204' may be about 10 μm in thickness. In some embodiments, either the PVDF or film is pattern coated with a very thin layer of medical grade polyurethane or acrylic adhesive. Acrylic may be less mobile in some embodiments and may be used to retain placement of the indicator to any underlying dressing structure.

Pattern-printed adhesive 106' may comprise various individual or composite adhesive materials, which may include, but are not limited to, acrylates or polyurethane adhesives. In some embodiments, pattern-printed adhesive 106' may be spaced to create a direct contact area of over 60% between buffer layer 204' and indicator 10' while pattern-printed adhesive 106' maintains only about 40% coverage of buffer layer 204' to adhere buffer layer 204' in place. In some embodiments, pattern-printed adhesive 106' may be a pattern of adhesive dots, lines, or grids 216 that achieve a direct contact area of over 60% between the buffer layer 204' and indicator 10' and only about 40% coverage of adhesive to retain buffer layer 204' in place. This ratio of 60% direct contact area to 40% adhesive coverage is designed to ensure sufficient moisture vapor transmission rate (MVTR) to allow for drying and re-setting of indicator 10'.

In some embodiments, buffer layer 204' may also be spray coated to top side 100' of indicator 10' in lieu of film retention adhesive 212'. Top side 100' of indicator 10' may also be a polyurethane film extruded onto PVDF 102' in a reel-to-reel process comprising thermal bonds between the two layers before an adhesive is added. In certain embodiments. PVDF 102' also may comprise a hydrophobic coating. In some embodiments, the PVDF layer may be plasma or otherwise coated with a hydrophobic coating which acts as a buffer to any fluids on a top surface.

Non-limiting examples of wound dressings 100 into which the indicator 10 described herein may be incorporated include, but are not limited to, a NANOVA™ wound dressing 100 available from Kinetic Concepts. Inc., of San Antonio: a TIELLE™ wound dressing 100 also available from Kinetic Concepts, Inc., a PICO wound dressing 100 available from Smith & Nephew, of the United Kingdom: an AQUACEL R wound dressing available from ConvaTec, of the United Kingdom: an AVELLE™ wound dressing, also available from ConvaTec: a GranuFoam R dressing available from Kinetic Concepts. Inc.: a V.A.C. VeraFlo R foam, also available from Kinetic Concepts. Inc.: ctc.

Methods of Use

Referring now to FIG. 6A-6C, a method of monitoring a patient's wound fluid status using wound dressing system 200 in accordance with the principles of the present disclosure is described. The method may include providing indicator 10' in fluid communication with wicking layer 214 of wound dressing system 200; exposing wound dressing system 200 to a first amount of fluid during the first state 110'; exposing wound dressing system 200 to a second amount of fluid during second state 112'; and exposing the wound dressing system 200 to a third amount of fluid during a third state. In first state 110', a marking 108' may be provided along the indicator 10' that is not visible to a user under ambient or natural light, but in second state 112', the marking 108' becomes visible to a user under ambient or natural light. In a third state, the marking 108' may again not be visible to a user under ambient or natural light, the third state occurring at a point in time subsequent to the second state 112'. In some embodiments, first state 110' corresponds to an initial application of the wound dressing system 200 and indicator 10' to a wound: second state 112' occurs in response to the wound dressing system 200 being exposed to fluid; and the third state occurs in response to some or all of the fluid to which the wound dressing system 200 was exposed in second state 112' being removed from or evaporating from wound dressing system 200.

Negative Pressure Wound Treatment Kit

Referring to FIGS. 7A-7B, a wound treatment kit. 300 for negative pressure wound treatment therapy in accordance with the principles of the present disclosure is described. Wound treatment kit 300 may include: (i) negative pressure source 302; (ii) wound dressing 304 configured to be attached to a patient wherein wound dressing 304 includes at least: (a) uncrosslinked silicone polymer adhesive 202: (b) indicator 10" comprising a top side, a bottom side and a buffer layer, wherein the top side comprises polyvinylidene difluoride (PVDF) and one or more markings configured to show fluid levels along a lower surface thereof, the bottom side comprises a pattern-printed adhesive, and buffer layer 204" is positioned between the silicone polymer adhesive 202" and the top side 100" of indicator 10", wherein buffer layer 204" comprises a top side comprising a polyurethane film and a bottom side comprising a film retention adhesive; and (iii) conduit 306 configured to fluidly couple negative pressure source 302 to a treatment space defined underneath wound dressing 304 upon application of wound dressing 304 to the patient. FIG. 7A depicts negative pressure wound treatment kit 300 in first state 110 wherein indicator 10 is not transparent due to the absence of wound exudate. FIG. 7B depicts wound treatment kit 300 in second state 112 wherein indicator 10 shows markings 108 due to the presence of wound exudate.

Referring again to FIGS. 7A-7B, wound treatment kit 300 further may include connector 314 configured to be sealed around opening 316 formed in drape layer 310 of wound dressing 304 to fluidly couple the negative pressure source 302 to the wound dressing 304, wherein indicator 10" is positioned between an upper surface 318 of the drape layer 310 and a lower surface of the connector 314. In some embodiments, wound treatment kit 300 further may include manifolding layer 308 configured to distribute negative pressure generated by the negative pressure source 302 to a wound located beneath the wound dressing 304. In some embodiments, wound treatment kit 300 also may include drape layer 310 configured to secure the manifolding layer 308 relative to the patient, wherein bottom side 104" of indicator 10" directly contacts manifolding layer 308. In further embodiments of wound treatment kit 300, top side 100" of indicator 10" directly contacts a lower surface 312 of drape layer 310 and bottom side 104" of the indicator 10" directly contacts periwound PW upon application of the wound dressing 304 to the patient.

Additional Embodiments

In some embodiments, the PVDF layer may be spray coated with a polyurethane gel which is then fully cured in place before it can be absorbed by the PVDF layer. This embodiment avoids the need for an adhesive layer and may least impact overall the moisture vapor transmission rate (MVTR) of the indicator.

EQUIVALENTS

Unless otherwise defined, all technical and scientific terms used herein have the same meaning as commonly understood by one of ordinary skill in the art to which this technology belongs.

As utilized herein, the terms "approximately," "about," "substantially", and similar terms are intended to have a broad meaning in harmony with the common and accepted usage by those of ordinary skill in the art to which the subject matter of this disclosure pertains. It should be understood by those of skill in the art who review this disclosure that these terms are intended to allow a description of certain features described and claimed without restricting the scope of these features to the precise numerical ranges provided. Accordingly, these terms should be interpreted as indicating that insubstantial or inconsequential modifications or alterations of the subject matter described and claimed are considered to be within the scope of the disclosure as recited in the appended claims.

Thus, it should be understood that the materials, methods, and examples provided here are representative of preferred aspects, are exemplary, and are not intended as limitations on the scope of the present technology. It should be noted that the term "exemplary" and variations thereof, as used herein to describe various embodiments, are intended to indicate that such embodiments are possible examples, representations, or illustrations of possible embodiments (and such terms are not intended to connote that such embodiments are necessarily extraordinary or superlative examples).

The present technology has been described broadly and generically herein. Each of the narrower species and sub-generic groupings falling within the generic disclosure also form part of the present technology. This includes the generic description of the present technology with a proviso or negative limitation removing any subject matter from the genus, regardless of whether or not the excised material is specifically recited herein.

The term "coupled" and variations thereof, as used herein, means the joining of two members directly or indirectly to one another. Such joining may be stationary (e.g., permanent or fixed) or moveable (e.g., removable or releasable). Such joining may be achieved with the two members coupled directly to each other, with the two members coupled to each other using a separate intervening member and any additional intermediate members coupled with one another, or with the two members coupled to each other using an intervening member that is integrally formed as a single unitary body with one of the two members. If "coupled" or variations thereof are modified by an additional term (e.g., directly coupled), the generic definition of "coupled" provided above is modified by the plain language meaning of the additional term (e.g., "directly coupled" means the joining of two members without any separate intervening member), resulting in a narrower definition than the generic definition of "coupled" provided above. Such coupling may be mechanical, electrical, or fluidic.

The term "or," as used herein, is used in its inclusive sense (and not in its exclusive sense) so that when used to connect a list of elements, the term "or" means one, some, or all of the elements in the list. Conjunctive language such as the phrase "at least one of X, Y, and Z," unless specifically stated otherwise, is understood to convey that an element may be either X, Y, Z; X and Y; X and Z; Y and Z; or X, Y, and Z (i.e., any combination of X, Y, and Z). Thus, such conjunctive language is not generally intended to imply that certain embodiments require at least one of X, at least one of Y, and at least one of Z to each be present, unless otherwise indicated.

References herein to the positions of elements (e.g., "top," "bottom," "above," "below") are merely used to describe the orientation of various elements in the FIGURES. It should be noted that the orientation of various elements may differ according to other exemplary embodiments, and that such variations are intended to be encompassed by the present disclosure.

In addition, where features or aspects of the present technology are described in terms of Markush groups, those skilled in the art will recognize that the present technology is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

Other aspects are set forth within the following claims.

What is claimed:

1. A wound dressing system, comprising:
an uncrosslinked silicone polymer adhesive; and
an indicator comprising a top side, a bottom side, and a buffer layer, wherein the top side comprises polyvinylidene difluoride (PVDF) and one or more markings configured to show fluid levels, the bottom side comprises a pattern-printed adhesive, and the buffer layer is positioned between the silicone polymer adhesive and the top side of the indicator, wherein the buffer layer further comprises a top side comprising a polyurethane film and a bottom side comprising a film retention adhesive.

2. The wound dressing system of claim 1, wherein the indicator further comprises a layer of wicking material.

3. The wound dressing system of claim 2, wherein the wicking material does not wick at least one of silicone oil, silicone gel, or a silicone derivative that when contacted with PVDF results in a change of states.

4. The wound dressing system of claim 2, wherein the wicking material is configured to wick exudate from a wound and the buffer layer is sized to prevent wicking from the uncrosslinked silicone polymer adhesive.

5. The wound dressing system of claim 1, wherein:
(i) in a first state, the marking is blocked by the top side PVDF and not visible to a user under ambient or natural light;

(ii) wherein in a second state, the marking is visible through the top side under ambient or natural light; and (iii) wherein in a third state, the marking is blocked by the top side and not visible to a user under ambient or natural light, the third state occurring at a point in time subsequent to the second state.

6. The wound dressing system of claim 5, wherein the first state is representative of an absence of absorbed wound fluid, the second state is representative of a presence of absorbed wound fluid, and the third state is representative of a reduction by evaporation of the wound fluid present in the second state.

7. The wound dressing system of claim 1, wherein the indicator is configured to reversibly undergo a first transition between a first visual configuration and a second visual configuration in response to the indicator being exposed to a first quantity of fluid, and to undergo a second transition between the second visual configuration and the first visual configuration in response to the indicator being exposed to a second quantity of fluid.

8. The wound dressing system of claim 1, wherein the indicator further comprises a portion comprising a fluid-impermeable material having a high moisture vapor transmission rate.

9. The wound dressing system of claim 1, wherein the buffer layer is about 10 μm in thickness.

10. The wound dressing system of claim 1, wherein the pattern-printed adhesive is spaced to create a direct contact area of over 60% between the buffer layer and the indicator and only about 40% coverage of adhesive to retain the buffer layer in place.

11. The wound dressing system of claim 1, wherein the buffer layer comprises a spray coating to the top side of the indicator in lieu of the film retention adhesive.

12. The wound dressing system of claim 1, wherein the top side of the indicator comprises a polyurethane film extruded onto the PVDF.

13. The wound dressing system of claim 1, wherein the PVDF further comprises a hydrophobic coating.

14. A method of monitoring a fluid status using the wound dressing system of claim 5, wherein the method comprises:

providing the indicator in fluid communication with a wicking layer of the wound dressing system;

exposing the wound dressing system to a first amount of fluid during the first state upon an initial application of the wound dressing system to a wound;

exposing the wound dressing system to a second amount of fluid during the second state after the initial application of the wound dressing system to the wound; and exposing the wound dressing system to a third amount of fluid during the third state after at least a portion of the second amount of fluid in the second state has been removed or evaporated from the wicking layer of the wound dressing system.

15. A wound treatment kit, comprising:

(i) a negative pressure source;

(ii) a wound dressing configured to be attached to a patient, wherein the wound dressing comprises: (a) an uncrosslinked silicone polymer adhesive; and (b) an indicator comprising a top side, a bottom side, and a buffer layer, wherein the top side comprises polyvinylidene difluoride (PVDF) and one or more markings configured to show fluid levels along a lower surface thereof, the bottom side comprises a pattern-printed adhesive, and the buffer layer is positioned between the silicone polymer adhesive and the top side of the indicator layer, wherein the buffer layer further comprises a top side comprising a polyurethane film and a bottom side comprising a film retention adhesive; and (iii) a conduit configured to fluidly couple the negative pressure source to a treatment space defined underneath the wound dressing upon application of the wound dressing to the patient.

16. The wound treatment kit of claim 15, wherein the kit further comprises:

a manifolding layer configured to distribute negative pressure generated by the negative pressure source to a wound located beneath the wound dressing; and a drape layer configured to secure the manifolding layer relative to the patient;

wherein the bottom side of the indicator directly contacts the manifolding layer.

17. The wound treatment kit of claim 16, wherein the top side of the indicator directly contacts a lower surface of the drape layer and the bottom side of the indicator directly contacts periwound upon application of the wound dressing to the patient.

* * * * *